United States Patent [19]

Lawson

[11] Patent Number: 5,258,532
[45] Date of Patent: Nov. 2, 1993

[54] COMPOUND, PREPARATION AND USE

[75] Inventor: John R. Lawson, Middleton, England

[73] Assignee: Imperial Chemical Industries PlC, London, England

[21] Appl. No.: 805,404

[22] Filed: Dec. 10, 1991

[30] Foreign Application Priority Data

Dec. 13, 1990 [GB] United Kingdom ............... 9027032

[51] Int. Cl.$^5$ ............... C07F 3/06; C07C 69/76; C07C 65/11
[52] U.S. Cl. ................... 556/132; 560/100; 562/467
[58] Field of Search ............ 556/132; 560/100; 562/467

[56] References Cited

U.S. PATENT DOCUMENTS

| | | | |
|---|---|---|---|
| 3,248,422 | 4/1966 | Elslager et al. | 260/520 |
| 4,304,707 | 12/1982 | Kuehn | 260/37 R |
| 4,329,381 | 5/1982 | Eschwey et al. | 427/386 |

FOREIGN PATENT DOCUMENTS

| | | |
|---|---|---|
| 0022701 | 1/1981 | European Pat. Off. . |
| 0115694 | 8/1984 | European Pat. Off. . |
| 0289155 | 11/1988 | European Pat. Off. . |
| 3306064 | 8/1984 | Fed. Rep. of Germany . |
| 1531093 | 11/1978 | United Kingdom . |
| 1555468 | 11/1979 | United Kingdom . |
| 1558411 | 1/1980 | United Kingdom . |

OTHER PUBLICATIONS

N. Kondekar et al., Condensation of 3-Hydroxy-2-naphthoic Acid with Formaldehyde, vol. 12, 1973, pp. 135-137, Industrial and Engineering Product Research Development.

*Primary Examiner*—Jose G. Dees
*Assistant Examiner*—Porfirio Nazario-Gonzalez
*Attorney, Agent, or Firm*—Cushman, Darby & Cushman

[57] ABSTRACT

A fused ring compound having hydroxy, carboxylic acid and hydroxyalkyl substituent groups and the metal salts or complexes thereof. The hydroxyalkyl group is especially a hydroxymethyl group. The compound is prepared by reaction of the hydroxy carboxylic acid derivative with formaldehyde in an alkaline medium at a temperature of not more than 50° C. The compounds, especially the metal salts or complexes thereof, can be used to provide corrosion inhibition of metals, for example iron.

13 Claims, No Drawings

COMPOUND, PREPARATION AND USE

The present invention relates to compounds, the preparation thereof and the use of such compounds, particularly in the treatment of metal surfaces to provide corrosion inhibition.

Corrosion of a metal may be reduced by coating the metal with an anti-corrosive coating composition, for example by coating iron and steel to reduce rusting. Metal surfaces exposed to weather are particularly vulnerable and require protection.

Anti-corrosive coating compositions are frequently based on film forming polymeric organic polymers and these typically also contain a mixture of pigments and extender solids, at least one of which is effective in retarding corrosion of the substrate metal. Pigments containing lead, in particular red lead, and hexavalent chromium, for instance zinc potassium chromate, are efficient anti-corrosive pigments and have been widely used with success. However, there is growing awareness of the toxicity of lead and hexavalent chromium and this has already resulted in some replacement of these materials by alternative materials. This trend is expected to accelerate when alternative materials are developed which have performance matching that of lead and hexavalent chromium. Zinc phosphate is considered non-toxic, and is extensively used as an anti-corrosive pigment. However, deficiencies in the performance of zinc phosphate are widely reported, in particular its inability to prevent rust creep from damages in the coating. Although slightly soluble metal salts of organic acids are extensively used as corrosion inhibiting additives in aqueous reservoir systems, surprisingly these materials are not widely used as corrosion inhibiting pigments in surface coating compositions. Pigments recently proposed as corrosion inhibitors in metal coating compositions, particularly for ferrous metals, include magnesium azelate (GB 1555468), zinc and lead 5-nitroisophthalates (GB 1531093), zinc cyanurate (U.S. Pat. No. 4329381) and zinc and lead N-phenylglycinate (DE 3306064). Barium salts of hydroxy carboxylic acids such as salicylic acid, have also been proposed (U.S. Pat. No. 4304707). However, barium salicylate is soluble in water at a level of greater than 10% w/w, and hence is liable to be leached from a coating containing barium salicylate. In European Patent Application Publication No. 0289155 there is described a surface-coating composition which contains, as a corrosion inhibitor, a salt of a metal (M) of a hydroxycarboxylic acid in which the hydroxy group and the carboxylic acid group are attached to the ring atoms of a fused ring system and wherein the metal M is at least divalent, for example the zinc salt of 3-hydroxy-2-naphthoic acid, 2-hydroxy-1-naphthoic acid or 1-hydroxy-2-naphthoic acid.

European Patent Application Publication No. 0022701 discloses poly(alkylene oxide) compositions containing a bridged dimer of a hydroxyl-substituted aromatic carboxylic acid or a salt thereof. The additives are stated to be highly efficient in inhibiting the oxidation of the poly(alkylene oxide) and also the corrosion of ferrous metals in contact therewith. Additives disclosed are the sodium salts of methylene disalicyclic acid, 5,5′-thiodisalicyclic acid and pamoic acid.

Whilst some of the foregoing systems provide good corrosion resistance, the search continues for alternative materials, particularly materials which provide improved properties.

We have now prepared compounds which can be used to provide useful corrosion resistance.

According to the present invention there is provided a compound having a fused aromatic ring system and hydroxy, carboxylic acid and hydroxyalkyl substituents attached to the ring atoms of the fused ring system and the salts or complexes thereof, wherein the hydroxy group and carboxylic acid group are attached to adjacent carbon atoms of the fused ring system and the hydroxyalkyl group is one in which the hydroxy group is attached to the carbon directly attached to the ring.

The fused ring system contains at least two rings fused together. One or more of the rings may contain a heteroatom, for example a nitrogen atom. Compounds in accordance with the present invention are particularly those in which at least one ring of the fused ring system is a hydrocarbon ring. The hydroxyalkyl group is conveniently attached to a ring atom adjacent to one to which either the hydroxy group or the carboxylic acid group is attached. We have obtained useful results when the fused ring system is a naphthalene ring system, as in 4-hydroxymethyl-3-hydroxy-2-naphthoic acid.

The compounds of the present invention are typically insoluble in an aqueous medium having a pH of below 7, for example about 3.5. The compounds of the present invention are typically solids having a melting point appreciably in excess of 250° C., for example 4-hydroxymethyl-3-hydroxy-2-naphthoic acid has a melting point of 285°–950° C. with some decomposition.

Salts or complexes can be obtained with metals or non-metallic groups such as ammonium or quaternary ammonium groups. The metal may be a monovalent metal such as sodium but metals of higher valency are generally less soluble in water and hence are preferred. The metal may be an alkali metal such as sodium or potassium or may be a metal of Group II of the Periodic Table such as magnesium, calcium, barium and zinc. A trivalent metal which may be used as the metal (M) is aluminium. We have obtained useful results using the zinc salt or complex of 4-hydroxymethyl-3-hydroxy-2-naphthoic acid.

Compounds in accordance with the present invention, particularly the salts or complexes thereof, can be coated onto a metal and we have found that the coated surface has an increased resistance to corrosion. The compounds, and the salts or complexes thereof, are suitable for the corrosion inhibition of iron, zinc, copper, tin and aluminium, particularly mild steel and the zinc surface of galvanised steel.

The compounds of the present invention can be obtained when the corresponding hydroxycarboxylic acid, for example 3-hydroxy-2-naphthoic acid, is reacted with an aldehyde at low temperature in non-acidic conditions.

More specifically a hydroxycarboxylic acid in which the hydroxy group and the carboxylic acid group are attached to the ring atoms of a fused ring system is reacted with an aldehyde at a temperature of not more than 50° C. in an aqueous medium having a pH of at least 7.

We have found that in acid medium, that is a pH of less than 7, essentially no reaction occurs at ambient temperature (about 20° C.) but on heating to a temperature of about 95° C. reaction occurs to produce a bridged dimer of the hydroxycarboxylic acid, for example 4,4′-methylene-bis(3-hydroxy-2-naphthoic acid)

with no detectable amount of a compound in accordance with the present invention.

We have found that at a pH only slightly above 7 reaction to form a compound in accordance with the present invention is generally slow. However, if the pH is 10 or higher, particularly at least 12, reaction occurs readily and formation of the hydroxyalkyl substituted compound may be essentially complete in a period of about one hour. If reaction at a pH of 10 or higher is continued for a prolonged period, for example more than 25 hours, the formation of a minor proportion of a bridged dimer of the hydroxycarboxylic acid is observed. However, if the mixture is heated to an elevated temperature, the formation of a bridged dimer is essentially complete in a time of about two hours.

The reaction is conveniently effected at a temperature of not more than 30° C., conveniently at ambient temperature (about 20° C.) or lower. At temperatures of above 50° C., especially above about 70° C., a bridged dimer is obtained. A minor proportion of a bridged dimer is also obtained if the reaction mixture is maintained at high pH, especially at least 12, for a prolonged period.

Hence, according to a preferred process in accordance with the present invention reaction is effected at a temperature in the range 0° to 30° C. for a period of from 0.5 to 5 hours in an aqueous medium having a pH of 10 or higher.

The aldehyde is conveniently formaldehyde and the product then obtained is a hydroxymethyl-substituted material. The aldehyde is preferably used in an amount of at least one mole for each mole of the hydrocarboxylic acid and an excess of the aldehyde is generally preferred, for example at least 1.05 moles of aldehyde for each mole of the hydroxycarboxylic acid. A large excess of aldehyde may be used but in general there is no significant advantage in doing so. Hence, the amount of the aldehyde typically does not exceed 10 moles, and especially is not more than 5 moles, for each mole of the hydroxycarboxylic acid. Very conveniently the aldehyde is used in an amount of from about 1.1 up to 2.5 moles for each mole of the hydroxycarboxylic acid.

Salts or complexes may be prepared by the reaction of the acid with a medium containing the desired cation. The salt or complex may be prepared as an aqueous solution by dissolving the acid in an aqueous medium containing the desired cation. However, many salt or complexes of the acid are of low water solubility and are not readily prepared in this manner. The acid is soluble in an aqueous medium of pH greater than 7 which contains monovalent cations, for example alkali metal ions. Hence, alkali metal salts or complexes may be obtained by dissolving the acid in an aqueous solution containing alkali metal cations and having a pH of greater than 7. The aqueous solution conveniently contains alkali metal carbonates and/or hydroxides.

Salts or complexes of metals other than the alkali metals are generally of low water solubility and are conveniently obtained by dissolving the acid in an aqueous alkaline solution containing an alkali metal and mixing the resulting solution with an aqueous solution containing the desired metal cation, for example zinc sulphate solution. The salt or complex formed is of low solubility and is precipitated. The precipitate can be separated in any suitable manner, for example by filtration. The solid may be washed and dried to remove water soluble impurities and subsequently the water. The reaction to form a salt or complex occurs readily at ambient temperature in the range 10° to 30° C.

A salt or complex of 4-hydroxymethyl-3-hydroxy-2-naphthoic acid with zinc contains two moles of the acid for each zinc atom. This material is of low solubility in water and has a melting point in excess of 300° C.

As noted previously herein, the compounds of the present invention can be used for the corrosion inhibition of metals. We have found that the water-insoluble salts or complexes with a metal give a particularly useful effect. As noted previously herein, many of the compounds and the salts or complexes thereof are solids which are not readily soluble in water. However, it is generally convenient to coat the compounds onto a metal surface from a liquid medium.

Hence, as a further aspect of the present invention there is provided a composition comprising a hydroxyalkyl hydroxycarboxylic acid compound as hereinbefore defined and a medium in which the said acid, salt or complex is present in solution, suspension or emulsion.

The medium is typically a liquid which may be an inorganic liquid such as water or an organic liquid such as an alcohol, ester, ether, ketone, aldehyde or the like. The medium may be a viscous medium such as a grease. The medium may be a coating composition such as a paint.

Thus, according to one specific aspect, the composition may be an aqueous emulsion or suspension of the acid, salt or complex. Aqueous emulsions or suspensions may be formed in the conventional manner and may include conventional dispersants and surfactants, including non-ionic dispersants.

The composition may alternatively include a surface coating compound or composition, for example a film forming binder system. The film forming binder system which can form a part of the composition may be a paint (primer), a lacquer; a resin or other protective coating. Thus, the surface coating composition may be a solvent-based composition, for example a cellulose/solvent based primer paint such as those used for car "touch up" paints. The acid, salt or complex of the present invention is generally insoluble in solvents used for such primers and typically is incorporated as a suspended solid, or pigment, in such a primer paint system. Alternatively, the surface coating composition may be an aqueous emulsion surface coating system, for example a primer or protective coating based on polymer latices such as for example acrylic and styrene/acrylic latices and vinyl acrylic copolymer latices including acrylate modified vinyl chloride - vinylidene chloride copolymer latices, and the acid, salt or complex may be used as a dispersion or suspension in such aqueous systems. The acid, salt or complex may also for example be incorporated in temporary alkali-removable protective coatings of the addition polymer type in which the polymer contains carboxyl groups.

If a film forming binder system is used, it is preferably one which contains an organic polymer and in general any such polymer used in the paint industry may be used. Thus, the suitable film forming binders include, for example, an alkyd resin, an epoxy resin, an oleoresin, a latex rubber, a chlorinated rubber, a vinyl resin such as polyvinylacetate or polyvinyl butyral, a polyurethane, a polyester, an organic or inorganic silicate, a polyamide or an acrylic polymer. It will be appreciated that two or more compatible film forming polymers may be used. The composition may also include an extender or plasticising resin, such as a hydrocarbon resin, or a coal tar derivative.

The film forming binder system which may be used can include homopolymers and copolymers of the following:
vinyl chloride,
vinylidene chloride,
vinyl esters of alkanoic acids having from 1 to 18 carbon atoms in the alkyl group, especially vinyl acetate, alkyl acrylates and methacrylates having from 1 to 18 carbon atoms in the alkyl group, acrylamide and substituted acrylamides, acrylonitrile, and methacrylonitrile, monoethylenically unsaturated hydrocarbons, for example ethylene, isobutene, styrene and alpha-methyl styrene.

Examples of polymers usable in a film forming binder system are "acrylic polymers", by which is meant those polymers comprising predominantly units of alkyl acrylates and/or methacrylates having from 1 to 12 carbon atoms in the alkyl group, sometimes containing an acid functionality by virtue of containing polymerised units of one or more aliphatic unsaturated alpha-beta unsaturated carboxylic acids. Polymers of this type are described in European Patent Application Publication No. 0115694.

Other examples of polymers usable in a film forming binder system are copolymers of (i) vinyl chloride, (ii) vinylidene chloride and (iii) one or more alkyl acrylates or alkyl methacrylates having from 1 to 12 carbon atoms in the alkyl group; such polymers may optionally also contain polymerised units of one or more aliphatic alpha-beta unsaturated carboxylic acids. Copolymers of this type are described generally and specifically in the specification of UK Patent No 1558411.

Alkyd containing resins are extensively used as the film forming binder in paint systems and a film forming binder system which is or contains an alkyd containing resin, particularly an oil-modified alkyd, can- be used.

The polymer or polymers, which is, or are, a component of a film forming binder system, is usually used in an amount of from 5 to 60% (based on the weight in grams of the polymer per 100 cm$^3$ of the film forming binder system), and more usually 10 to 40%. The polymer may be dissolved or colloidally dispersed (that is exist as an emulsion, with an average particle size usually below two micrometers) in a suitable liquid carrier medium.

The medium in which the acid, salt or complex is present in solution, suspension or emulsion may be any material which can be applied to a surface to provide a coating thereon. Thus, the medium may be a natural oil or a natural grease which has been derived from animals or plants, such as, for example, lanolin or rape seed oil. Alternatively, the medium may be a petroleum refined product such as a lubricating oil, turbine oil, fuel oil, gasohol or grease, which are used in circumstances in which they contact, and coat, if only temporarily, a metal surface.

The composition which comprises the acid, salt or complex in a liquid or other medium may be coated onto a metal surface to provide a corrosion inhibiting coating. This treatment may be combined with a conventional corrosion inhibition treatment such as, for example, the phosphating of iron. The composition may include, in addition to the acid, salt or complex, other materials, particularly those which have been proposed as corrosion inhibitors. Thus, the composition may include a metal oxide, and if the composition contains a salt or complex of the acid the oxide may be an oxide of a metal which is the same as the metal which is present in the salt or complex, for example zinc. As an alternative to, or in addition to, a metal oxide, the composition may also include a metal phosphate, particularly a phosphate of a metal which is the same as that present in the salt or complex.

Blends containing the acid, salt or complex of the present invention together with a metal oxide and/or a metal phosphate can be prepared by any suitable mixing technique. Such blends may be preformed and the blend may then by incorporated into a composition containing the blend and a film forming binder system. Alternatively, the components of the blend may be added separately to a film forming binder system in order to prepare a composition which may be coated onto a metal.

A composition containing the acid, salt or complex typically contains from 0.1 to 30% by weight of the acid, salt or complex relative to the total volume of the composition and preferably the acid, salt or complex is present in an amount of 0.1 to 5% w/v. If the composition is an emulsion of a film forming binder system in a liquid medium, the acid, salt or complex may give a useful effect when dispersed in the emulsion in an amount of from 0.1 to 15% w/v. If a metal oxide and/or phosphate is also present in the composition, it is preferred that the total of acid, salt or complex plus the metal oxide and/or phosphate does not exceed 70% w/v.

In addition to the acid, salt or complex and optionally the metal oxide and/or the metal phosphate, a surface coating compound or composition may include various other ingredients commonly employed in film forming compositions such as defoamers, rheology control agents, thickeners, dispersing and stabilising agents (usually surfactants), wetting agents, extenders, fungicides, pigments or colourants of one sort or another, coalescing solvents, plasticisers, and anti-freeze agents.

A composition containing an acid, salt or complex of the present invention may be prepared using any of the techniques which have been used for incorporating solids into a liquid or plastic medium in which the solid is essentially insoluble. Thus, if the composition is based on a film forming binder system, techniques for preparing paint compositions may be used, for example by mixing the components either in a grinding apparatus or premixing the components and then grinding. The acid, salt or complex and any optional other corrosion inhibitor such as a metal oxide or phosphate, may be incorporated into the surface coating composition at any convenient stage, for example during the grinding together of the components of the paint formulation.

As noted previously herein, the acid, salt or complex of the present invention may be coated onto a metal, particularly to provide a corrosion inhibiting coating on the metal.

Thus, as a further aspect of the present invention there is provided a process which comprises coating at least part of a surface of a metal with an acid, salt or complex as hereinbefore defined.

The process of the present invention results in a coated surface which typically has an increased resistance to corrosion and is especially suitable for the corrosion inhibition of iron, zinc, copper, tin, and aluminium, particularly mild steel and the zinc surface of a galvanised steel.

A composition containing the acid, salt or complex may be applied to a metal surface in conventional manner, for example by dipping, spraying or brushing. The temperature of the application may be any suitable temperature, for example from 0° to 50° C.

The metal surface which is coated may be brightly polished and/or freshly cleaned, but a lightly rusted surface may be coated by the process of the present invention. Thus the acid, salt or complex may be coated onto a surface in an "as received" condition, and it may be unnecessary for the surface to be freshly cleaned or brightly polished. Such a procedure provides a corrosion inhibiting coating on the surface of a metal and may be combined with conventional corrosion inhibition treatments such as the phosphating of iron.

The coating process of the present invention may be used as the only corrosion inhibition treatment and the metal may not be subjected to a further treatment. Alternatively, the coating process may be a pre-treatment applied to a metal surface before the application of a known surface coating. If desired the coating process may be used to provide temporary protection whilst the metal is being transferred from one site to another and the protective coating subsequently removed before or during further processing.

It is a particular feature of this aspect of the present invention to contact a metal surface with a salt or complex, particularly a zinc salt or complex, in suspension in a liquid medium, particularly an aqueous medium. We have found that a metal surface which has been contacted in the foregoing manner shows improved corrosion resistance. Such a procedure can be used alone or may be combined with one or more subsequent stages in which a surface coating composition, typically a paint, is applied to the surface. A metal surface coated in this manner shows a reduced amount of blistering of the paint surface and a decreased amount of through rusting.

Thus, as a further aspect of the present invention there is provided a metal article, at least part of one surface of which has a coating which is, or which contains, an acid, salt or complex as hereinbefore defined.

The metal article may have a single surface coating which is, or which contains, an acid, salt or complex as hereinbefore defined. Thus, the surface of the metal may be coated with an acid, salt or complex as hereinbefore defined or with a surface coating composition, for example a paint or the like, which contains an acid, salt or complex as hereinbefore defined. The metal surface may have a coating of several layers, at least one of which contains the acid, salt or complex and it is generally preferred that at least the layer directly in contact with the metal surface is, or contains, an acid, salt or complex as hereinbefore defined.

Various aspects of the present invention are set out in more detail hereafter in the following illustrative examples in which all parts and percentages are by weight unless otherwise stated.

EXAMPLE 1

60.8 parts of 3-hydroxy-2-naphthoic acid (obtained from Hoechst GmbH) were stirred with 400 parts of distilled water. 56 parts of a concentrated aqueous solution of sodium hydroxide containing 47% w/w of sodium hydroxide were added, and the mixture stirred whilst heating to 70° C., at which temperature a clear solution was obtained. The solution had a pH of 12.5. This solution was cooled to 10°±2° C. and 31 parts of an aqueous solution of formaldehyde (37% w/w) were added over about 30 seconds whilst continuing stirring and cooling. The temperature rose to 14° C. during the next five minutes, and was subsequently maintained at 15°±2° C.

After stirring for three hours at 15°±2° C., the reaction mixture was poured into 500 parts of cold (10° C.) water and 120 parts of aqueous 5N sulphuric acid was added to give a pH of about 3.5. A suspension was formed and this was stirred at 15°±5° C. for 30 minutes, and then filtered. The filtercake was washed with approximately 300 parts of cold (10° C.) water, and dried in vacuo (20-25 Torr) at 20°±5° C. for 24 hours. The product (71.6 parts, 98.6% of theory, mpt 285-95(d)) was found by analysis to contain: C,63.4% by wt and H,4.7% by wt. 4-Hydroxymethyl-3-hydroxy-2-naphthoic acid ($C_{12}H_{10}O_4.0.5H_2O$) requires C,63.4% by wt and H,4.8% by wt.

Proton NMR using deuterated dimethylsulphoxide as solvent and tetramethyl silane as internal reference gave shifts of 5.0 (s, 2H, —$CH_2$—O); and 7.4–8.5 (m, 5H, (aromatic), splitting pattern consistent with assigned structure). By mass spectroscopy a fragment of mass/charge ratio 218 was detected, this being consistent with 4-hydroxymethyl-3-hydroxy-2-naphthoic acid.

EXAMPLE 2

2.27 parts of 4-hydroxymethyl-3-hydroxy-2-naphthoic acid, prepared as described in Example 1, were stirred with 7 parts of distilled water, and 0.85 parts of sodium hydrogen carbonate were added. After stirring at 20°±3° C. for about 20 minutes a few drops of aqueous 2N sodium carbonate were added giving a clear solution of pH 8.8. A solution was prepared separately by stirring 2 parts of zinc sulphate heptahydrate (obtained from Aldrich Chemical Company Ltd) with 4 parts of water.

The two aqueous solutions were then mixed and stirred at 20°±5° C. for one hour. A pale cream suspension formed immediately on mixing the solutions and the resulting mixture was filtered. The filtercake was washed with 30 parts of cold (10° C.) water and dried in vacuo (20-25 Torr) at 20°±5° C. for 24 hours.

The product obtained (1.69 parts, 62.7% of theory, mpt >300° C.) was found by analysis to contain: C,53.4% by wt; E,3.4% by wt; and Zn,12.3% by wt. The zinc salt of 4-hydroxymethyl-3-hydroxy-2-naphthoic acid of stoichiometry ($C_{12}H_9O_4)_2$. Zn.2.2 $H_2O$ requires: C,53.4% by wt, H4.2% by wt; and Zn,12.1% by wt.

Experiment 1

Stability Test 2.18 parts of the product of Example 1 were stirred with 20 parts of aqueous N sodium hydroxide solution giving a solution of pH 12.6. Stirring was continued for one hour at 20°±5° C. After this time, High Performance Liquid Chromatography (HPLC), using an HP 1090 instrument obtained from Hewlett Packard plc, indicated that the starting material was unchanged. The temperature of the reaction mixture was then quickly raised to 75°±50° C. and stirring was continued for two hours. After this time HPLC indicated almost complete conversion to 4,4'-methylene bis (3-hydroxy-2-naphthoic acid). In Table One are set out the relative proportions of 4-hydroxymethyl-3-hydroxy-2-naphthoic acid and 4,4'-methylene bis (3-hydroxy-2-naphthoic acid) as determined by HPLC on samples taken after various times at pH 12.6 and 75°±5° C.

TABLE ONE

| COMPONENT | % (by HPLC) at time (mins) | | | | | |
|---|---|---|---|---|---|---|
| | 0 | 20 | 40 | 60 | 80 | 120 |
| 4-Hydroxymethyl-3-hydroxy-2-naphthoic acid | 100 | 29 | 8 | 4 | 3 | 2 |
| 4,4'-methylene bis (3-hydroxy-2-naphthoic acid) | 0 | 71 | 91 | 96 | 97 | 98 |

The reaction mixture was cooled to 20°±5° C. and acidified to PE 4 by addition of 1.5 parts of glacial acetic acid. A yellow suspension formed and was filtered, washed with 100 parts of cold (10° C.) water, and dried in vacuo (20-25 Torr) at 20°±5° C. for 24 hours. The yield of dry product was 1.82 parts (93% of theory—mpt 298°-305° C. (d)). By analysis, the product was found to contain:C,70.4% by wt. and H,4.2% by wt. 4,4'-methylene bis (3-hydroxy-2-naphthoic acid) $C_{23}H_{16}O_6.0.22H_2O$ requires C,70.4%; and H,4.2% by wt.

Proton NMR using deuterated dimethylsulphoxide as solvent and tetramethyl silane as internal reference gave shifts of 4.8 (s, 2H, —$CH_2$—); and 7.2-8.5 (m, 10H, aromatics, splitting pattern consistent with assigned structure). By mass spectroscopy a fragment of mass/charge ratio 388 was detected, this being consistent with 4,4'-methylene bis (3-hydroxy-2-naphthoic acid).

COMPARATIVE EXAMPLE A 1.9 parts of 3-hydroxy-2-naphthoic acid were stirred with 80 parts of water and 9 parts of aqueous N sodium hydroxide solution. The partial solution thus produced was stirred at 20°±5° C. and 3 parts of aqueous 2N sodium carbonate solution were added in small portions over about one hour, eventually producing a clear solution at pH 7.8. One part of aqueous formaldehyde solution (containing 37% w/w formaldehyde) was added all at once and the reaction mixture was stirred at 20°±5° C. for two hours, then a further one part of aqueous formaldehyde was added. Stirring was continued at 20°±5° C. for 22 hours, when EPLC indicated only slight conversion of 3-hydroxy-2-naphthoic acid to 4-hydroxymethyl-3-hydroxy-2-naphthoic acid. Ten parts of aqueous N sodium hydroxide solution were then added, producing a pH of 12.3 in the solution and stirring was continued at 20°±5° C. After one hour, HPLC indicated almost total reaction to 4-hydroxymethyl-3-hydroxy-2-naphthoic acid. Stirring was continued at 20°±5° C. for a further 27 hours, when HPLC indicated the presence of both 4-hydroxymethyl-3-hydroxy-2-naphthoic acid (81%) and 4,4'-methylene bis (3-hydroxy-2-naphthoic acid) (19%). The temperature of the mixture was raised to 90°±5° C. After stirring at 90±5° C. for two hours, HPLC indicated that conversion of 4-hydroxymethyl-3-hydroxy-2-naphthoic acid to 4,4'-methylene bis (3-hydroxy-2-naphthoic acid) was essentially complete. The reaction mixture was cooled to 20°±5° C. and acidified with 1.5 parts of glacial acetic acid. The product was isolated by filtering, washing the filtercake with 50 parts of cold (10° C.) water, and drying in vacuo (20-25 Torr) for 24 hours at 20°±5° C. The yield of 4,4'methylene bis (3-hydroxy-2-naphthoic acid) was 1.85 g (95% of theory—mpt 295°-310° C. (d)). This material was identical with the product of Experiment-I by i.r, NMR, and HPLC.

Samples were removed from the reaction mixture at various times and the composition of each sample was determined by HPLC. The relative proportions of 3-hydroxy-2-naphthoic acid, 4-hydroxymethyl-3-hydroxy-2-naphthoic acid and 4,4'-methylene bis (3-hydroxy-2-naphthoic acid) are set out in Table Two.

TABLE TWO

| COMPONENT | % (by HPLC) at time (hrs) | | | | | | |
|---|---|---|---|---|---|---|---|
| | 0 | 4 | 22* | 23 | 27** | 49 | 51 | 53 |
| 3-hydroxy-2-naphthoic acid | 100 | 100 | 93 | 4 | 0 | 0 | 0 | 0 |
| 4-hydroxymethyl-3-hydroxy-2-naphthoic acid | 0 | tr | 7 | 96 | 93 | 81 | 13 | 4 |
| 4,4'-methylene bis (3-hydroxy-2-naphthoic acid) | 0 | 0 | 0 | tr | 7 | 19 | 87 | 96 |

Notes to Table Two
*pH of solution raised to 12.3
**Temperature raised to 90 ± 5° C.

COMPARATIVE EXAMPLE B

The procedure described incorporates the method of Kondekar, and Potnis; Ind. Eng. Chem. Prod. Res. Develop. 12(2), 135-7 (1973).

1.9 parts of 3-hydroxy-2-naphthoic acid were stirred with 25 parts of glacial acetic acid and 25 parts of water at 20°±5° C. and 2 parts of aqueous formaldehyde solution (37% w/w) were added. After stirring at 20°±5° C. for 24 hours, HPLC indicated that no reaction had occurred. The reaction flask was then heated up to 95°±5° C. and stirred at that temperature for 7 hrs. After that time, EPLC indicated complete conversion to 4,4' methylene bis (3-hydroxy-2-naphthoic acid). There was no evidence of the formation of 4-hydroxymethyl-3-hydroxy-2-naphthoic acid during this reaction.

COMPARATIVE EXAMPLE C 3.9 parts of 4,4'-methylene bis (3-hydroxy-2-naphthoic acid), prepared as described in Comparative Example B, were stirred with 200 parts of water and 18 parts of aqueous N sodium hydroxide solution. The pH of the solution/suspension was maintained at between 7.5 and 8.0 by gradual addition of 1.5 parts of aqueous 2N sodium carbonate, until a clear solution was obtained. Separately, 2.88 parts of zinc sulphate heptahydrate, were stirred with 30 parts of water to give a clear solution. The two solutions were mixed and stirred at 20°±5° C. for 2 hours. The suspension obtained was filtered, washed with 100 parts of cold (10° C.) water and dried in vacuo (20-25 Torr) at 20°±5° C. for 24 hours. The product (1.97 parts, 33% of theory, mpt >300° C.) was found b analysis to contain: C,46.2% by wt; H,3.0% by wt; and Zn,24.0% by wt. A zinc complex of the stoichiometry $C_{23}H_{14}O_6Zn_{2.2}(OH)_22H_2O$ requires: C,46.0% by wt; H,3.3% by wt; and Zn,24.0% by wt.

COMPARATIVE EXAMPLE D 1.94 parts of 4,4'-methylene bis (3-hydroxy-2-naphthoic acid) were stirred with 100 parts of water and 9.8 parts of aqueous N sodium hydroxide solution, to give a clear solution at pH 7.8.

Separately, 1.44 parts of zinc sulphate heptahydrate were stirred with 15 parts of water to give a clear solution. The two solutions were then mixed and stirred at 20°±5° C. for 2 hours. A pale yellow suspension was formed which was heated to 90°±5° C. and stirred for 10 minutes then cooled to 20°±5° C. and filtered. The filtercake was washed with 100 parts of cold (10° C.) water and dried in vacuo (20–25 Torr) at 20°±5° C. for 24 hours.

The product (1.98 parts, 66% of theory, Mpt >300° C.) was found by analysis to contain: C,58.1% by wt; H,3.6% by wt; and Zn,13.3% by wt. A zinc complex of stoichiometry $C_{23}H_{14}O_6.Zn.1.33H_2O$ requires C,58.1% by wt; H,3.5% by wt; and Zn,13.8% by wt.

EXAMPLE 3

0.25 parts of the zinc salt of 4-hydroxymethyl-3-hydroxy-2-naphthoic acid, prepared as described in Example 2, were stirred with 100 parts of distilled water for 30 minutes at 20°±5° C. The suspension thus formed was diluted to 400 parts with distilled water, and 50 parts of an aqueous solution containing 30% w/v sodium chloride were added. The total volume was then adjusted to 500 parts with distilled water.

Cold-rolled panels of mild-steel measuring 15.24 cm ×10.16 cm ×0.25 mm (6×4×0.01 inches) reference no D-46, obtained from Q-Panel Company Ltd were cut into small coupons measuring approximately 5 cm ×2 cm. A hole was punched into each coupon about 5mm from one of the shorter edges in a central position. These coupons were degreased by immersion in boiling 1,1,1-trichloroethane liquid and vapour and allowed to cool. Each coupon was accurately weighed and then suspended from a glass support in 250 parts of a liquid medium. Duplicate experiments were performed in each of which the liquid medium was the suspension containing the product of Example 2. Two control experiments were carried out-in each of which the liquid medium was a solution containing 3% w/v sodium chloride. The coupons were allowed to remain immersed in the liquid medium at 20°±5° C., replenishing evaporated water at convenient intervals. After seven days, the coupons were removed. Any corrosion products adhering to the surface of the coupons were removed by gently rubbing with a soft tissue, then immersing in concentrated aqueous 10N hydrochloric acid for five seconds at 20°±5° C., followed immediately by rinsing in water. After rinsing in acetone and drying in a stream of air, the coupon was reweighed. The degree of protection afforded by the inhibitor was calculated from the following equation $$\% \text{ Protection} = 1 - \frac{\% \text{ wt loss treated panel}}{\% \text{ wt loss control panel}} \times 100$$

Results are given in Table Three.

COMPARATIVE EXAMPLES E–G

Reservoir corrosion tests were carried out exactly as described in Example 3 except that the product of Example 2 was replaced by the zinc salt of 3-hydroxy-2-naphthoic acid, prepared as described in European Patent Application Publication No 289155 (Comparative Example E), or the product of Comparative Example C (Comparative Example F) or the product of Comparative Example D (Comparative Example G). Results are given in Table Three.

TABLE THREE

| EXAMPLE OR COMP EX | % PROTECTION | | | | MEAN VALUE |
|---|---|---|---|---|---|
| | 1 | 2 | 3 | 4 | |
| 3 | 94 | 93 | 94 | 94 | 94% |
| E | 86 | 86.5 | 76 | 87 | 84% |
| F | 30 | 33 | 5 | — | 23% |

TABLE THREE-continued

| EXAMPLE OR COMP EX | % PROTECTION | | | | MEAN VALUE |
|---|---|---|---|---|---|
| | 1 | 2 | 3 | 4 | |
| G | 78 | 76 | 75 | — | 76% |

EXAMPLE 4

Corrosion inhibitor test method. Metal coupons were evaluated by the Salensky method described in "Corrosion Control by Organic Coatings", Salensky, G. A.; National Association of Corrosion Engineers, 1981, Leidheiser, E. Jr (Ed).

Cold-rolled coupons of mild steel measuring approximately 4 cm ×1.5 cm were cut from the larger panels described in Example 3. Each coupon was degreased as described in Example 3 and stored in a clean, dry container. Each coupon was weighed accurately and placed in a pyrex test-tube measuring 250 mm ×25 mm i.d. (Quickfit reference MF 24/3 (24/29)). 10 parts of di(2-ethylhexyl)phthalate and 2 parts of a 3% w/v aqueous solution of sodium chloride were then added, followed by 0.027 parts of the product of Example 2. The test-tube was sealed with a ground-glass socket (Quickfit reference ST 53/13) fitted with a screw-on cap and glass tube (i.d. 6 mm), thus allowing ingress of air without permitting splashing or excessive evaporation of the contents of the test-tube. The assembly was clamped into a Laboratory Flask Shaker, (SFI) obtained from Stuart Scientific Ltd, and agitation commenced (control setting 8). After 44 hours at 20°±5° C., the shaker was stopped and the coupon removed and cleaned as described in Example 3. The test-panel was then reweighed. Duplicate tests were carried out, as well as duplicate control experiments. The procedure was repeated using different proportions of the product of Example 2. The degree of protection was calculated as described in Example 3. Results are given in Table Four.

COMPARATIVE EXAMPLES H TO J

The procedure described in Example 4 was repeated, except that the product of Example 2 was replaced by various proportions of either zinc-bis(2-hydroxy-3-naphthoate) (Comparative Example H), or of the product of Comparative Example C (Comparative Example I) or of the product of Comparative Example D (Comparative Example J).

The results obtained are given in Table Four.

TABLE FOUR

| Ligand Concentration (m mol dm$^{-3}$) | % Protection afforded using ligand type (a) | | | |
|---|---|---|---|---|
| | 2 | ZB | C | D |
| 20 | 97 | 98 | 90 | 93 |
| 10 | 94 | 83 | 91 | 90 |
| 5 | 84 | 72 | 84 | 85 |
| 1 | 81 | 68 | 34 | 10 |
| 0.5 | 3 | 0 | 2 | 8 |
| 0.1 | 0 | 0 | — | — |

Notes to Table Four
(a) 2, C & D are the products of Example 2 and Comparative Examples C & D respectively.
ZB is the zinc salt of 3-hydroxy-2-naphthoic acid.

EXAMPLE 5

1.0 part of the product of Example 2 was stirred with 16 parts of Industrial methylated spirits and 4 parts of tripropyleneglycolmethylether, (DOWANOL TPM obtained from the Dow Chemical Company) were added. Approximately 30 glass beads, 2mm in diameter were also added, and the suspension, in a tightly stoppered bottle, was placed on a roller mill rotating at 60 r.p.m. for 24 hours. A mild-steel Q-panel as described in Example 3 was degreased as described in Example 3-. The suspension of the product of Example 2, prepared as described above, and separated from the glass beads, was applied to the steel panel using a coating-bar (K-bar No 8-100 micrometers) and the solvent allowed to dry at 20°±5° C. for 24 hours. One coat of a quick-drying zinc phosphate alkyd-based primer was then applied by brushing to give an even coating of approximately 50 micrometers thickness when dried. After storage for ten days at 20°±5° C., the panel was scribed and subjected to ASTM B117 salt spray testing for 1000 hours. Results of the test are given in Table Five.

COMPARATIVE EXAMPLES K TO N

The procedure of Example 5 was repeated, with the exception that the product of Example 2 was replaced by the same proportion by weight of either zinc bis(3-hydroxy-2-naphthoate) (Comparative Example K), or of the product of Comparative Example C (Comparative Example L), or the product of Comparative Example D (Comparative Example M). The results obtained are given in Table Five.

A further comparison (Comparative Example N) was carried out in which the coating with the suspension of the additive was omitted and the panel was coated with one coat of a quick-drying zinc phosphate alkyd-based primer as described in Example 5. This coated panel was also scribed and subjected to the ASTM B117 salt-spray test for 1000 hours. Results are given in Table Five.

In the foregoing tests, three techniques were used to assess the degree of corrosion resistance offered by the pretreatment/primer paint systems or the primer paint system alone during the salt-spray testing (ASTM B 117):

1. Rust width ("W in Table Five); the figure given denotes the maximum rust width (in mm) around the original scribe-line; the lower this value, the better the system is in resisting corrosion after physical damage to the paint-coating.
2. Blistering ("B" in Table five) denotes the degree and type of blistering which is apparent under the paint surface. The ratings were assessed by comparison to standards given in ASTM D714-87.
3. Through-rusting ("R" in Table Five): The degree and type of through-rusting was assessed by the method of F. A. Champion ("Corrosion Testing Procedures" Second Edition, Chapman and Hall (1964) pp 197-279) using the comparative standards given in this reference.

TABLE FIVE

| EXAMPLE OR COMP EX | Assessment of Paint-film performance in ASTM B117 salt-spray after: | | | | | | | | |
|---|---|---|---|---|---|---|---|---|---|
| | 300 hrs | | | 600 hrs | | | 1000 hrs | | |
| | W | B | R | W | B | R | W | B | R |
| 5 | 2 | 10 | 0 | 2 | 10 | 0 | 2 | 10 | 0 |
| K | 1 | 10 | 0 | 6 | 10 | 0 | 10 | 2VF | 0 |
| L | 0 | 10 | 0 | 2 | 10 | 0 | 3 | 10 | 0 |
| M | 1 | 6F | 2 | 16 | 3M | 3 | 23 | 1MD | 3 |
| N | 1 | 10 | 0 | 13 | 2F | 0 | 24 | 1M | 0 |

Notes to Table Five
VF is very few
F is few
M is medium
MD is medium dense

I claim:
1. A naphthalene compound having hydroxy, carboxylic acid and hydroxyalkyl substituents attached to the ring atoms of the naphthalene ring and the salts and complexes thereof wherein the hydroxy group and carboxylic acid group are attached to adjacent carbon atoms of the naphthalene ring and the hydroxyalkyl group is one in which the hydroxy group is attached to the carbon atom directly attached to the ring.
2. The compound of claim 1 wherein the hydroxyalkyl group is attached to a ring atom adjacent to one to which the hydroxy or the carboxylic acid group is attached.
3. The compound of claim 1 wherein the hydroxyalkyl group and hydroxy group are attached to adjacent carbon atoms.
4. The compound of claim 1 wherein the fused aromatic ring system is a naphthalene ring.
5. The compound of claim 1 wherein the hydroxyalkyl group is hydroxymethyl.
6. A salt or complex of a compound as claimed in claim 1 obtained from a metal of Group II of the Periodic Table.
7. The compound 4-hydroxymethyl-3-hydroxy-2-naphthoic acid.
8. A sodium or zinc salt or a zinc complex of 4-hydroxymethyl-3-hydroxy-2-naphthoic acid.
9. A process for preparing a naphthalene compound having hydroxy, carboxylic acid and hydroxyalkyl substituents attached to the ring atoms of the naphthalene ring and wherein the hydroxy group and carboxylic acid group are attached to adjacent carbon atoms of the naphthalene ring and the hydroxyalkyl group is one in which the hydroxy group is attached to the carbon directly attached to the ring comprising the reaction of a hydroxycarboxylic acid in which the hydroxy and carboxylic acid groups are attached to the ring atoms of a naphthalene ring with an aldehyde at a temperature of not more than 50° C. in an aqueous medium having a pH of at least 7.
10. The process of claim 9 wherein the pH is 10 or higher.
11. The process of claim 9 wherein the temperature is not more than 30° C.
12. The process of claim 9 wherein the hydroxycarboxylic acid is reacted with the aldehyde at a temperature in the range 0° to 30° C. for a period of from 0.5 to 5 hours in an aqueous medium having a pH of 10 or higher.
13. The process of claim 9 wherein the aldehyde is formaldehyde.

* * * * *